United States Patent
Cronin et al.

(10) Patent No.: US 10,656,695 B2
(45) Date of Patent: May 19, 2020

(54) HEALTH WEARABLE THAT AUTOMATICALLY CHANGES SENSOR READING TIMINGS

(71) Applicant: KONINKLIJKE PHILIPS N.V., Eindhoven (NL)

(72) Inventors: John Cronin, Bonita Springs, FL (US); Michael G. D'Andrea, Burlington, VT (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 150 days.

(21) Appl. No.: 15/559,453

(22) PCT Filed: Mar. 25, 2016

(86) PCT No.: PCT/IB2016/051705
§ 371 (c)(1),
(2) Date: Sep. 19, 2017

(87) PCT Pub. No.: WO2016/151539
PCT Pub. Date: Sep. 29, 2016

(65) Prior Publication Data
US 2018/0113498 A1    Apr. 26, 2018

Related U.S. Application Data

(60) Provisional application No. 62/138,260, filed on Mar. 25, 2015.

(51) Int. Cl.
*G06F 1/26* (2006.01)
*G06F 1/32* (2019.01)
(Continued)

(52) U.S. Cl.
CPC .......... *G06F 1/3206* (2013.01); *A61B 5/0205* (2013.01); *A61B 5/1118* (2013.01);
(Continued)

(58) Field of Classification Search
None
See application file for complete search history.

(56) References Cited

U.S. PATENT DOCUMENTS 7,647,131 B1 * 1/2010 Sadowski .......... G05B 23/0297
700/108
2013/0191662 A1   7/2013 Ingrassia, Jr.
(Continued)

OTHER PUBLICATIONS

Observations on the PCT International Search Report and the Written Opinion of International Application No. PCT/IB2016/051705, Bond, Schoeneck & King, PLLC, dated Sep. 2, 2016.
(Continued)

*Primary Examiner* — Nitin C Patel

(57) ABSTRACT

System and a method wherein a wearable device receives sensor data at a wearable device and compares a first value determined from the sensor data with a second value determined from the sensor data to determine a percentage change in the sensor data from the first sample to the second sample. The system and method may also change a sampling frequency of the sensor at the wearable device according to one or more settings that were set by a user of the wearable device. The system and method optimizes power consumption while optimally recording data sensed by one or more sensors at a wearable device.

13 Claims, 11 Drawing Sheets

(51) Int. Cl.
    *G06F 1/3206*     (2019.01)
    *A61B 5/0205*     (2006.01)
    *A61B 5/11*     (2006.01)
    *A61B 5/00*     (2006.01)
    *G06F 1/3212*     (2019.01)
    *G06F 1/324*     (2019.01)

(52) U.S. Cl.
    CPC .......... *A61B 5/6804* (2013.01); *G06F 1/3212* (2013.01); *A61B 2560/0209* (2013.01); *G06F 1/324* (2013.01); *Y02D 10/126* (2018.01); *Y02D 10/174* (2018.01)

(56) References Cited

U.S. PATENT DOCUMENTS

| | | | |
|---|---|---|---|
| 2014/0183386 A1* | 7/2014 | Ravid | G06F 17/00 251/129.01 |
| 2014/0358472 A1 | 12/2014 | Goel | |
| 2015/0057967 A1 | 2/2015 | Albinali | |
| 2016/0094796 A1* | 3/2016 | Govil | H04N 5/3456 348/295 |
| 2016/0142508 A1* | 5/2016 | Ishihara | H04L 67/2842 370/236 |

OTHER PUBLICATIONS

PCT International Search Report, International Application No. PCT/IB2016/051705, dated Mar. 25, 2016.

* cited by examiner

| Sensor Data | | | |
|---|---|---|---|
| Time | Sensor 1 Pulse | Battery level | Battery Level Calculator Data |
| 8:00AM | 81bpm | 90% | 8.0 hours |
| 8:01AM | 81bpm | 90% | 8.0 hours |
| 8:02AM | 81bpm | 90% | 7.9 hours |
| 8:03AM | 82bpm | 89% | 7.9 hours |
| 8:04AM | 84bpm | 89% | 7.9 hours |
| 8:05AM | 85bpm | 89% | 7.9 hours |
| 8:06AM | 86bpm | 88% | 7.8 hours |
| 8:07AM | 86bpm | 88% | 7.8 hours |
| 8:08AM | 86bpm | 88% | 7.8 hours |
| ..... | | | |
| 9:10AM | 81bpm | 79% | 7.5 hours |
| 9:11AM | 81bpm | 79% | 7.5 hours |

| Pulse Sensor Frequency | Battery Life Estimate | User Settings |
|---|---|---|
| 10 Seconds | 8 hours | Maximum |
| 1 Minute | 48 hours | |
| 2 Minutes | 96 hours | |
| 5 Minutes | 240 hours | Default |
| 10 Minutes | 480 hours | |
| 15 Minutes | 720 hours | Minimum |
| 30 Minutes | 1540 hours | |
| | | |
| Battery Life Setting | Max | |
| | | |
| Alert Type | Text | |

| Charging Window | | |
|---|---|---|
| Day | Start Time | Stop Time |
| Monday | 6:00PM | 8:00PM |
| Tuesday | Null | Null |
| Wednesday | 6:00PM | 8:00PM |
| Thursday | Null | Null |
| Friday | 6:00PM | 8:00PM |
| Saturday | Null | Null |
| Sunday | Null | Null |

FIG. 10

HEALTH WEARABLE THAT AUTOMATICALLY CHANGES SENSOR READING TIMINGS

CROSS-REFERENCE TO RELATED APPLICATIONS

This application claims the priority benefit under 35 U.S.C. § 371 of international Patent Application No. PCT/IB2016/051705, files Mar. 25, 2016, which claims priority to U.S. Provisional Patent Application Ser. No. 62/138,260, filed on Mar. 25, 2015. These applications are hereby incorporated by reference herein in their entirety.

FIELD OF THE INVENTION

The present invention generally relates to system and method for a wearable device receiving sensor data from a sensor. More specifically, the wearable device may determine when to change a sample rate of sensor data from the sensor in order to limit power consumption.

BACKGROUND

Wearables are mobile electronic devices that are worn on the body, or attached to or embedded in clothes and accessories. These mini computers and sensors can display, process, and/or gather information, and tend to have wireless communication capabilities.

Presently, available electronic sensors coupled to a computing device are used to collect and manipulate data sensed by the electronic sensors. Sensors that sense acceleration are used to collect data relating to motions of a person wearing a wearable electronic device. For example, certain devices have accelerometer sensors that count a number of steps by measuring acceleration in three dimensions (X, Y, and Z) during an activity (e.g., walking). Some wearable devices allow the user operating a GUI in an app or web app to enter other data related to primary parameters (e.g., number of calories consumed). In such devices, sensor data and user input may be stored in memory and used by a processor to calculate calories burned or weight lost.

In such computing devices, the sensor data sensed by the sensor may be stored in memory, and a processor running an algorithm may identify patterns in the data that corresponds to a series of sensations sensed by the sensors. Wearable computing devices coupled to sensors may also be used to sense the activity of a person wearing the computing device when exercising. Wearable device may also make measure physiological parameters of a person. Examples of physiological parameters that may be measured include, yet are not limited to, blood pressure, heart rate, blood oxygen level, and blood sugar level. In certain instances, such products may determine whether a person is running or walking based on data sensed by the sensors. This may be done based on counting steps, where the data is sensed by an acceleration sensor over a period of time.

However, currently available wearable devices do not monitor power consumption and modify parameters affecting power consumption according to current power usage and a time when a battery in the wearable device is scheduled be recharged. Accordingly, there is a need in the art for a system and method for monitoring and modifying parameters relating to power consumption such that a wearable device can reduce power consumption while still continuing to operate until a scheduled time.

SUMMARY OF THE INVENTION

Accordingly, various embodiments disclosed herein include a system and a method where a wearable device receives sensor data and saves the received sensor data in a memory at the wearable device. In various embodiments, the system and method may compare a first sample of sensor data with a second sample of sensor data when determining a percentage change in the sensor data from the first sample to the second sample. In other embodiments, the system and method may change a sampling frequency of the sensor at the wearable device according to one or more settings that were set by a user of the wearable device.

In embodiments disclosed herein, the system and methods may decrease the frequency of sampling data from the sensor when the percentage change in data sensed by the sensor is below a threshold level. Alternatively when the percentage change in data sensed by the sensor is above a threshold level, the sampling frequency of sampling data from the sensor may be increased.

According to an aspect, a method for monitoring power consumption at a wearable device, the method comprises: receiving a plurality of sensor samples from a sensor at the wearable device, the sensor sampling at sampling frequency; determining at least a first sensor value and a second sensor value from the plurality of sensor samples; calculating a difference between the first sensor value and the second sensor value; and varying the sampling frequency according to the calculated difference between the first sensor value and the second sensor value.

According to an embodiment, the first value is a magnitude of a first sample of the plurality of sensor samples and the second value is a magnitude of a second sample of the plurality of sensor samples.

According to an embodiment, the first value is a time elapsed between a first event measured by the plurality of sensors and a second event measured by the plurality of sensor samples, and the second value is a time elapsed between a third event measured by the plurality of sensors and a fourth event measured by the plurality of sensor samples.

According to an embodiment, the third event and the second event are the same.

According to an embodiment, the sampling frequency is increased if the percentage difference is above a predetermined threshold.

According to an embodiment, the sampling frequency is increased if the percentage difference is above a predetermined threshold and the second value is greater than the first value.

According to an embodiment, the sampling frequency is decreased if the percentage difference is above a predetermined threshold and the second value is less than the first value.

According to an embodiment, the sampling frequency is decreased if the percentage difference is below a predetermined threshold.

According to an embodiment, the method further comprises the steps of: estimating the remaining charge time of a battery of the wearable device; comparing the remaining charge time to a time until next charge; decreasing the sampling rate of the sensor upon determining that the remaining charge time is less than the time until next charge.

According to an embodiment, the time until next charge is calculated according to a next charge time received from a user.

According to another aspect, a non-transitory computer readable storage medium having embodied thereon a program executable by a processor to perform an algorithm, the algorithm comprising the steps of: receiving a plurality of sensor samples from a sensor at the wearable device, the sensor sampling at sampling frequency; determining at least a first value and a second value from the plurality of sensor samples; varying the sampling frequency according to the percentage difference between the first value and the second value.

According to an embodiment, the first value is a magnitude of a first sample of the plurality of sensor samples and the second value is a magnitude of a second sample of the plurality of sensor samples.

According to an embodiment, the first value is a time elapsed between a first event measured by the plurality of sensors and a second event measured by the plurality of sensor samples, and the second value is a time elapsed between a third event measured by the plurality of sensors and a fourth event measured by the plurality of sensor samples.

According to an embodiment, the third event and the second event are the same.

According to an embodiment, the sampling frequency is increased if the percentage difference is above a predetermined threshold.

According to an embodiment, the sampling frequency is increased if the percentage difference is above a predetermined threshold and the second value is greater than the first value.

According to an embodiment, the sampling frequency is decreased if the percentage difference is above a predetermined threshold and the second value is less than the first value.

According to an embodiment, the sampling frequency is decreased if the percentage difference is below a predetermined threshold.

According to an embodiment, the algorithm further comprises the steps of: estimating the remaining charge time of a battery of the wearable device; comparing the remaining charge time to a time until next charge; decreasing the sampling rate of the sensor upon determining that the remaining charge time is less than the time until next charge.

According to an embodiment, the time until next charge is calculated according to a next charge time received from a user.

As used herein for purposes of the present disclosure, the term "controller" is used generally to describe various apparatus relating to the operation of a ventilator apparatus, system, or method. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 10 is a table of settings that may be saved in a smart charging database, according to an embodiment.

DETAILED DESCRIPTION OF EXEMPLARY EMBODIMENTS

Exemplary embodiments disclosed and described herein include a system and method that adjusts the sampling rate of at least one sensor according to contextual requirements, in order to preserve battery life. In an embodiment, the device may change the sampling rate of the sensor by calculating a ratio between (otherwise described in this disclosure as a percentage change) a first value and a second value, as measured by the sensor. In an embodiment a sampling frequency of the sensor may be changed according to one or more settings that were set by a user of the wearable device.

Figure 1:
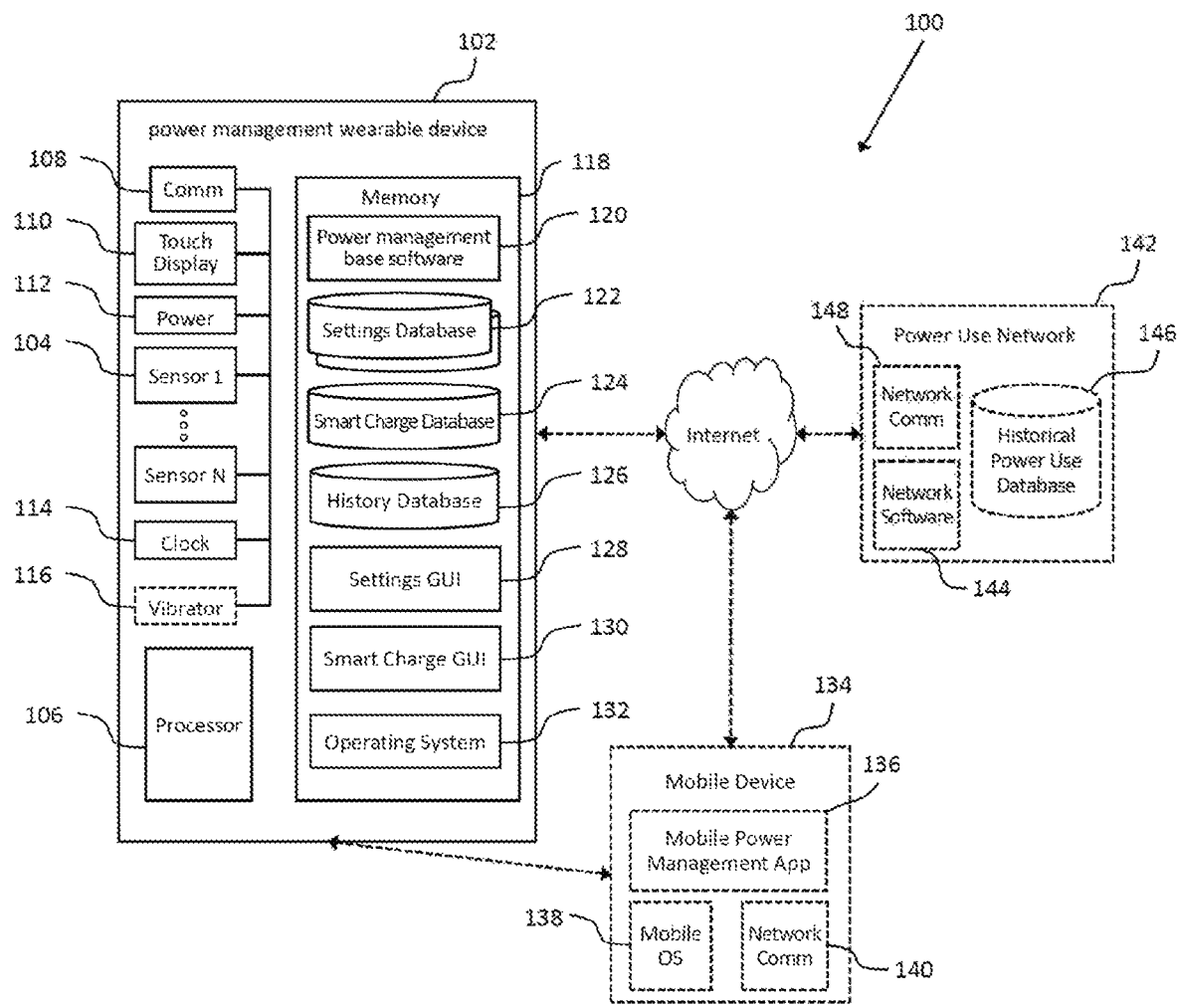
FIG. 1 illustrates a system for adjusting a sensor sampling frequency, according to an embodiment.

Referring now to FIG. 1, there is shown an embodiment of a wearable device 102 architecture having a plurality of sensors: sensors 1-N. At least one sensor of sensor 1-N, discussed herein as sensor 104, may be sampled at a predetermined sampling rate, resulting in a plurality of sensor measurements. From these measurements, at least a first value and a second value may be determined. The sampling rate may be adjusted (either faster or slower) according to the percentage change between the first value and the second value. For example, if a light sensor, sampling at a predetermined sampling rate, measures a low light for the first sample and a bright light for the second sample, there will be a large percentage change between the samples and the sampling rate may accordingly be increased. Similarly, a measured bright light followed by a low light will result in a large percentage change and an increase in sampling rate. Conversely, if a low light is measured for the first sample, and a similarly low light is measured for the second sample, there will be a low percentage change between the samples, and therefore the sampling rate may remain the same or decreased.

According to an embodiment, sensor 104 is in continuous or periodic communication with processor 106. In an embodiment, processor 106 may instruct sensor 104 to sample a certain frequency. Alternately, processor 106 may drive sensor 104 for each sample (processor 106 thereby setting the sampling frequency according to the frequency that it instructs sensor 104 to sample). In an alternate embodiment, processor 106 may instruct an intermediate component to drive sensor 104 at a particular sampling frequency. One of ordinary skill in the art will appreciate, in conjunction with a review of this disclosure, that the sampling frequency of the sensor 104 may be set and executed by any method as is known in the art for setting the sampling frequency of a sensor 104. Furthermore, in an embodiment, processor 106 may perform the calculations, although one of ordinary skill will appreciate that each sensor 104 may be equipped with the computational power necessary to perform the required calculation. Alternately, the calculations may be performed by a paired local device or by a remote server.

In an embodiment, a sampling frequency of sensor 104 may be decreased when the percentage change in data sensed by the sensor 104 is below a predetermined threshold. Conversely, when the percentage change in data is above a predetermined threshold, the sampling frequency may be increased. For example, if the predetermined threshold is a 5% change with respect to a previous measured value, and the second measured value represents a 7% change compared to the first measured value, the sampling frequency may be increased because 7% is above the 5% threshold. In an embodiment, when the percentage change is above or below the predetermined threshold, the sampling frequency may be increased or decreased by a predetermined amount, respectively. For example, if the percentage change is an increase of 7% and thus above the example predetermined threshold of 5% the sampling rate may be increased a predetermined 20%. By contrast, if the percentage change is beneath the 5% threshold (in an embodiment), the sampling rate may be decreased 20%.

One of ordinary skill will appreciate, in varying embodiments, that multiple thresholds may be implemented and associated with multiple rates of increase or decrease. For example, a change above a 5% threshold may result in 10% sampling rate increase, while a change above a 10% threshold may result in a 15% increase (alternately, a change below the 5% percent threshold may result in a 7% decrease). Furthermore, the thresholds for increasing the sampling rate may be different than those for decreasing the sampling rate. For example, anything below a 5% percentage change may result in a decreased sampling rate, while anything above a 7% percentage change may result in an increased sampling rate, and anything in between may result in no change in sampling rate. One of ordinary skill will appreciate, in conjunction with a review of this disclosure that the thresholds and/or amount increase are a matter of design choice and will vary according to the kind of sensor, implementation, measurement, and context of use, among other design considerations.

Alternatively, the sampling rate may be increased/decreased in direct proportion to the percentage change. For example, a 5% percentage change may result in a 5% increase sampling rate. Alternatively, a multiplier may be applied to the percentage change, or some other mathematical operation may be applied to the percentage change to result in the increase/decrease in sampling rate. This may be applied in conjunction with a threshold as described above. For example, the sampling rate may be increased in proportion to the percentage change of the measured values for any percentage change above 5%.

It will be appreciated by a person of ordinary skill, in conjunction with a review of this disclosure, that the identity of the compared values may vary between kinds of sensors and kinds of measurements. For instance, some sensors merely measure a magnitude. For example, a light sensor may measure a magnitude (i.e. brightness) of received light for a given sample. Thus, the magnitude of sensed light of each sample may be compared, and the sample rate adjusted accordingly. However, other sensors are used to measure quantities beyond simple magnitudes, such as the time elapsed between identifiable events. For example, a heart rate monitor may measure the time elapsed between plurality of heartbeats (i.e. identifiable events) to deduce a heart rate. In other words, a heart rate monitor may measure the time elapsed between two or more events as measured across at least two samples. Thus, when comparing the percentage change in sensor data for a heart monitor, it may be necessary to measure the percentage change in time elapsed between three or more events (i.e. the percentage change in the time elapsed between a first and second measured event and the time elapsed between the second and third measured event).

In an example, if a sensor 104 at the wearable device 102 senses a consistent heart rate of the user of the wearable device 102, the sampling frequency of the heart rate sensor 104 may be reduced. If the user of the wearable device 102 then begins to exercise (e.g. start running) after detecting an increase in heart rate, the sampling frequency of the heart rate sensor 104 may be increased until such time that a variability in the heart rate sensed stabilizes. Thus, in an embodiment, the device (or system) may collect more sensor data when the sensor data changes most and store less sensor data when the sensor data changes the least, thus managing power while recording data at eventful times.

In an embodiment, if a future charging time is known—or may otherwise be estimated—the power requirements of sensor 104 may be adjusted in order to ensure that the battery charge may last till the next charging time. In other words, when the battery charge is projected to be exhausted before a scheduled or estimated charging time, the sampling frequency of data from the sensor 104 may be automatically adjusted such that the battery should be able to sustain operation of the wearable device 102 until the scheduled or estimated charging time. In an embodiment, in the event that software running on a processor determines that the wearable device 102 is unlikely to sustain operation of the wearable device 102 until the scheduled charge time a message may be sent to the user of the wearable device 102 indicating that the user should either charge the battery at the wearable device 102 or change power consumption settings set at the wearable device 102. In an embodiment, the next charging time may be estimated by monitoring the typical use of the wearable device 102 (i.e. tracking the times that a wearable device 102 is charged), in order to estimate the next likely charging time. In an alternate embodiment, the user may affirmatively input the next charging window.

In an embodiment, sample rates may be affirmatively set according to one or more settings set at a wearable device 102 or at a mobile device that communicates with the wearable device 102. Settings set at the wearable device 102 or at the wearable device 102 may also identify how much the sample rate of one or more sensors may be adjusted automatically over time. Settings set by a user of the wearable device 102 may also maintain current sampling frequencies when sensor data is within a range. For example, the heart rate sensor 104 may be sampled at a current sample rate when the heart rate is above a threshold level.

Referring again to FIG. 1, there is shown an embodiment of a system for automatically changing sensor reading timings. FIG. 1 includes a power management wearable device 102, a power use network, and a mobile device 134 that may communicate with each other over the Internet. In alternate or additional embodiments, wearable device 102 and mobile device 134 may communicate over Bluetooth, low-power Bluetooth, Wi-Fi, laser, visible, infrared, microwave, and/or any other suitable method for communicating wirelessly and/or via a wired connection such as an Ethernet port, a USB port, etc. The power management wearable device 102 may also communicate with the mobile device directly over a wireless data communication interface or via a connection with a cable. In an embodiment, the power management wearable device 102 includes at least a communication interface 108, a touch display 110, a power supply 112, sensors 1-N (including sensor 104), a clock 114, a vibrator 116, and a memory 118. Vibrator 116 may be utilized to notify a user to change settings or reduce activity (as is discussed below). In an alternate embodiment, the user may be notified by a speaker configured to emit a sound, or through an SMS, e-mail, or other notifications means as are known in the art. The memory 118 may include, for example, power management base software 120, a settings database 122, a smart charge database 124, a history database 126, a settings GUI 128, a smart charge GUI 130, and operating system software 132.

In an embodiment, the mobile device 134 in FIG. 1 may include a mobile power management application 136, a mobile operating system 138 (OS), and a network communication interface 140. The power use network 142 includes network software 144, a historical power use database 146, and a network communication interface 148.

The system can also be integrated with a mobile phone (e.g. mobile device 134) or other mobile device where some or all of the GUIs and notifications are located on the phone. In this instance the wearable device 102 could be very simple and not include a display, for example. Further, the power management program could be located on a mobile phone and used to operate 1-N sensors. In this instance the wearable device 102 may not require a large or need a powerful processor that would otherwise be necessary to run the various power management programs described herein. This would be ideal for use with energy harvesting sensors. In yet another embodiment, network databases could be utilized to enhance the functionality of the power management program by downloading data about variations of specific variables. For example, heart rate may be associated with specific benchmarks that indicate sleep. An individual of a certain age and health may use the downloaded data to identify how the sensor frequency may be varied over time to provide the greatest utility while managing power use at the wearable device 102.

Figure 2:
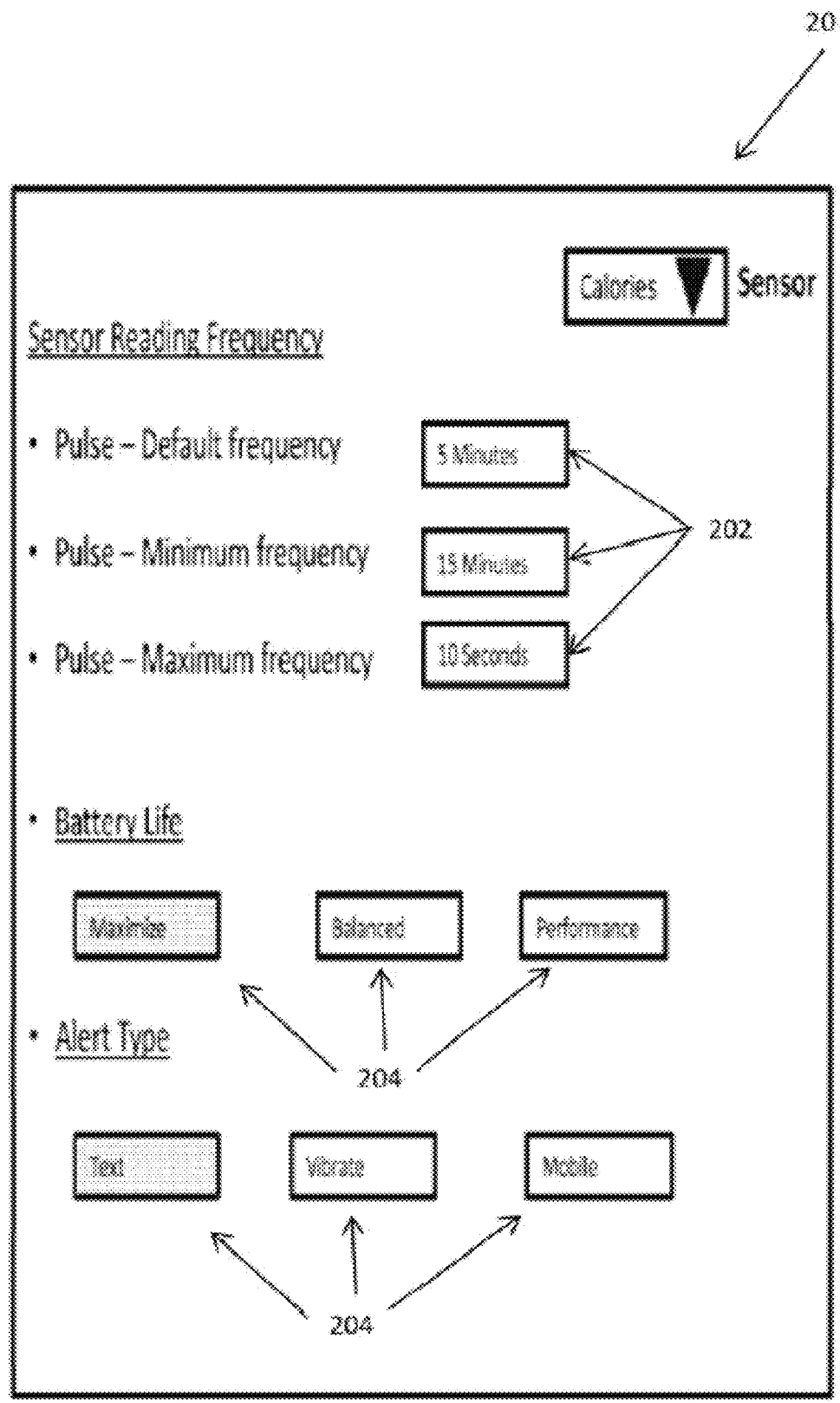
FIG. 2 illustrates a settings GUI that may be displayed on a display, according to an embodiment.

FIG. 2 illustrates just one embodiment of a settings GUI 200 that may be displayed on a display. The setting GUI 200 may reside in memory on the mobile device 134 or may reside in memory at the wearable device 102. In an embodiment, the settings GUI may include several different data entry boxes 202 and different selection boxes 204. The data entry boxes 202 may be used when configuring how frequently a sensor (e.g. sensor 104) will be polled for data. For example, the settings GUI may allow the user to set a pulse default frequency that has a setting of 5 minutes, a pulse minimum frequency that has a setting of 15 minutes, and a maximum pulse freely of 10 seconds. Selection boxes 204 in the GUI may include battery life selection boxes and an alert type selection box. The battery life selection boxes may be used to select a low power setting that corresponds to maximizing batter life. Alternatively battery life may be set to be balanced, which may optimize both sensor sensitivity and battery life, or be set in a performance mode which may set sensors to a high or maximum sensitivity (i.e. sampled often). The alert type selection box may allow a user to configure an alert such as a text message, a vibration, or an alert sent to the mobile device. FIG. 2 also identifies a calorie sensor.

When the battery life selection box is set to performance the pulse rate of a user of the wearable device may be sensed at a maximum, or otherwise high, frequency. When the battery life is set to a balanced level, the pulse rate of the user may be sensed at a default frequency. When the pulse rate is set to maximum the pulse rate of the user may be sensed at a minimum frequency. Power use will correspond to how frequently the sensors at the wearable device 102 are used. The less frequent a sensor is used the less power the wearable device 102 will consume.

Figure 3:
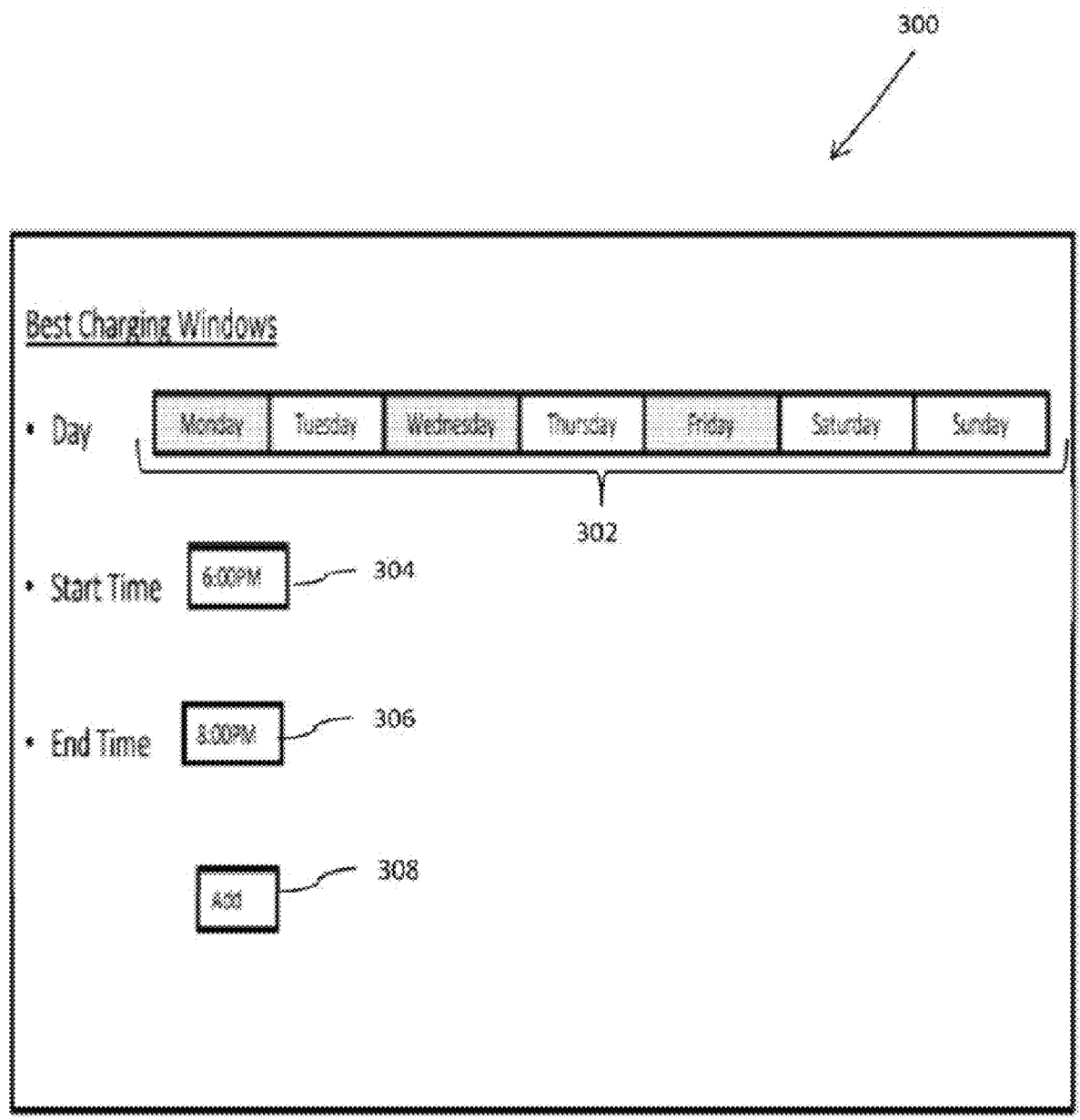
FIG. 3 illustrates a smart charging GUI that may be displayed on a display, according to an embodiment.

FIG. 3 illustrates an embodiment of a smart charging GUI 300 that may be displayed on a display. The smart charging GUI 300 may be stored in memory at the wearable device 102 or be stored in memory at the mobile device 134. The GUI includes boxes 302 that identify days of the week (Monday through Sunday). In an embodiment, the grayed out selection boxes of Monday, Wednesday, and Friday indicate that those days are identified as having a charging window. The GUI 300 identifies a start time 304 of 6:00 PM and an end time 306 of 8:00 PM corresponding to a best timing charging window on Monday, Wednesday, and Friday. Additional times may be entered into the GUI by selecting the add selection box 308 in the GUI.

Figures 4A, 4B:
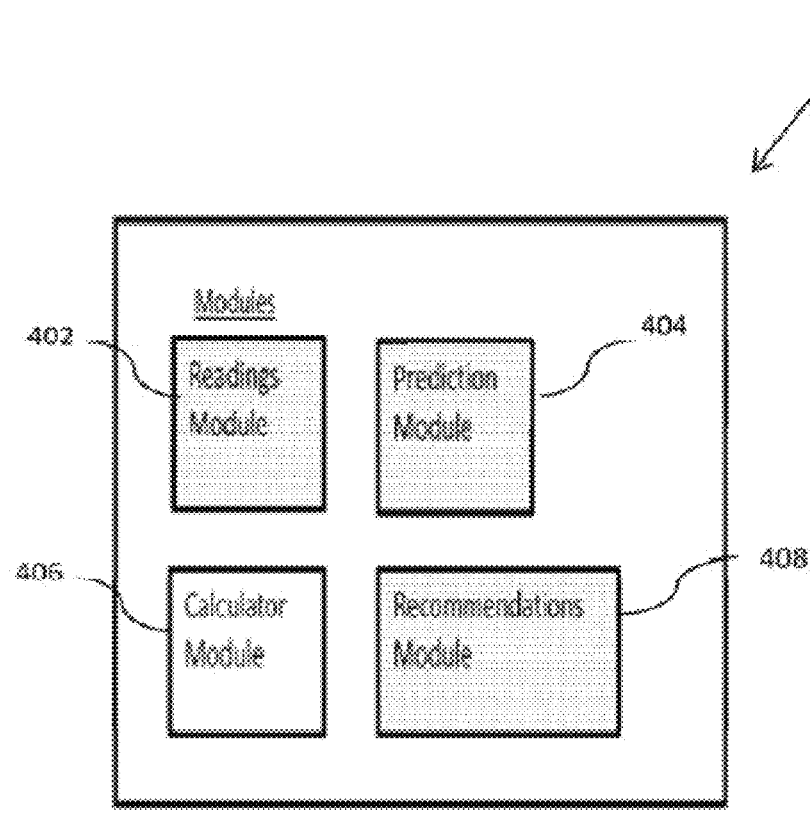
FIG. 4A illustrates power management base software comprising software modules, according to an embodiment.
FIG. 4B is a flowchart of a power management base method, according to an embodiment.

FIG. 4A illustrates an embodiment of software modules that may be include in power management base software. The software modules depicted in FIG. 4A are a readings module 402 configured to adjust the sensor sampling frequency dynamically according to context, a prediction module 404 configured to estimate the time until the next charge window, a calculator module 406 configured to calculate remaining battery life, and a recommendations module 408 configured to adjust sensor 104 sampling according to user-defined settings or notify the user to change the user-defined settings.

FIG. 4B illustrates an embodiment of a program flow 410 that the power management base software 120 may execute. In an embodiment, the program flow 410 of the power management software 120 in FIG. 4B may begin in a first step, step 412, that may execute program code from the calculator module to calculate remaining battery life. In step 414, the program code of the readings module may be executed to adjust the sensor sampling frequency dynamically according to context. In step 416, the program code of the prediction module may be executed to estimate the time until the next charge window. And in step 418 the program code of the recommendations module may be executed adjust sensor 104 sampling according to user-defined settings or notify the user to change the user-defined settings.

Figure 5:
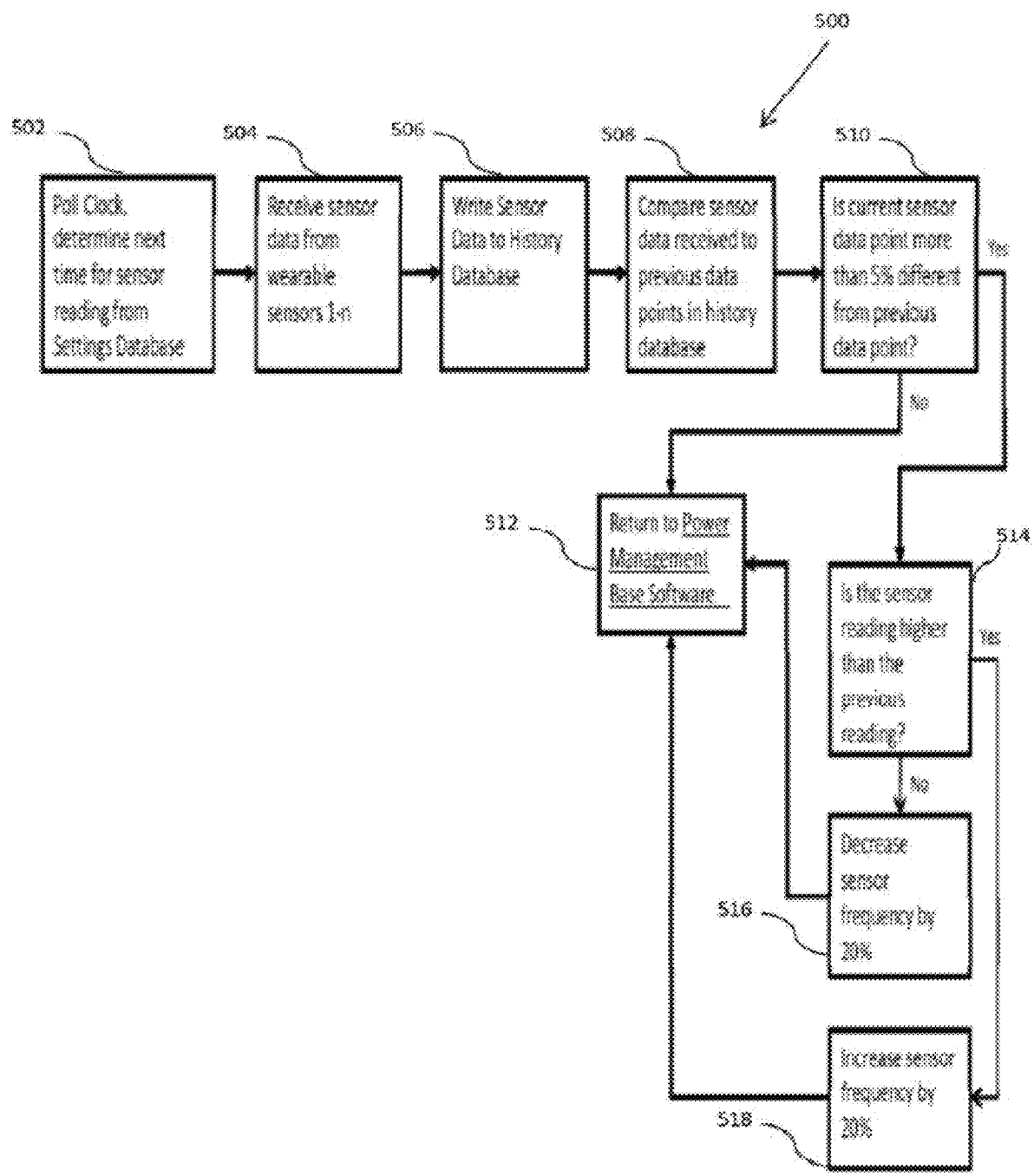
FIG. 5 is a flowchart of an algorithm that may be implemented by a readings module of power management base software, according to an embodiment.

FIG. 5 illustrates a flowchart of an embodiment of an algorithm 500 implemented by the readings module. In step 502, a clock may be polled for a time. This step may also determine a next time when time for inputting (reading) sensor data by querying a settings database. One of ordinary skill will appreciate, in conjunction with a review of this disclosure, that in another embodiment, a clock signal may drive the sensors and determine the next sampling time without requiring a polling step. In step 504, sensor data may be received from sensors 1 though N. In step 506, the sensor data may be written in a database. In step 508, the received sensor data may be compared to previous data stored in the history database.

In an embodiment, in step 510 of the algorithm of FIG. 5 currently measured sensor data may be compared to determine whether it is within 5% of sensor data previously received. One of ordinary skill will appreciate, in conjunction with a review of this disclosure, that this step may include the step of comparing a first measured value with a second measured value, each measured value being determined from the received sensor data (e.g., an elapsed time between positive events detected with the measured sensor data). When the sensor data—or measured value—is within 5% of previously received sensor data, program flow may return to executing power management base software 120 (i.e. sampling the sensor at a default or previously set rate) at step 512. When the sensor data or measured value is more than 5% of sensor data that was previously received, program flow may move to step 514 that determines whether the current sensor reading is higher than a previous sensor reading. If no—e.g., the second measured value is at least 5% less than the first measured value—the sensor sampling frequency may be decreased by 20% at step 516. After decreasing the sensor sampling frequency program flow moves to the step 512 where the power management base software is executed with the new sampling frequency. If the current sensor reading is higher than the previous reading—e.g., the second measured value is at least 5% more than the first measured value—program flow moves to step 518 where the sensor sampling frequency is increased by 20%. After increasing the sensor sampling frequency, program flow moves to the step where the power management base software is executed with the new sampling frequency. In an alternate embodiment, the sampling frequency may be increased (or decreased) for any change in value above (or below) the threshold, regardless of whether the second value or data point is higher or lower than the first. The details of the implementation of this method are discussed more fully above.

This system/device can be utilized in a multi-sensor system and the user may be allowed to set parameters for each sensor. The user may also prioritize the use of the sensors. For example a calorie counter could be added to this system with its own minimum, maximum, and default frequency. The sensors could also be prioritized. For example the calorie counter frequency may be reduced (turned down) first before altering a pulse sensor at the wearable device 102.

In an embodiment, the readings module software of FIG. 5 can be configured to adjust the sensor sampling frequency dynamically such that a sensor will be monitored less frequently or more frequently based on settings that may be set in a GUI.

Figure 6:
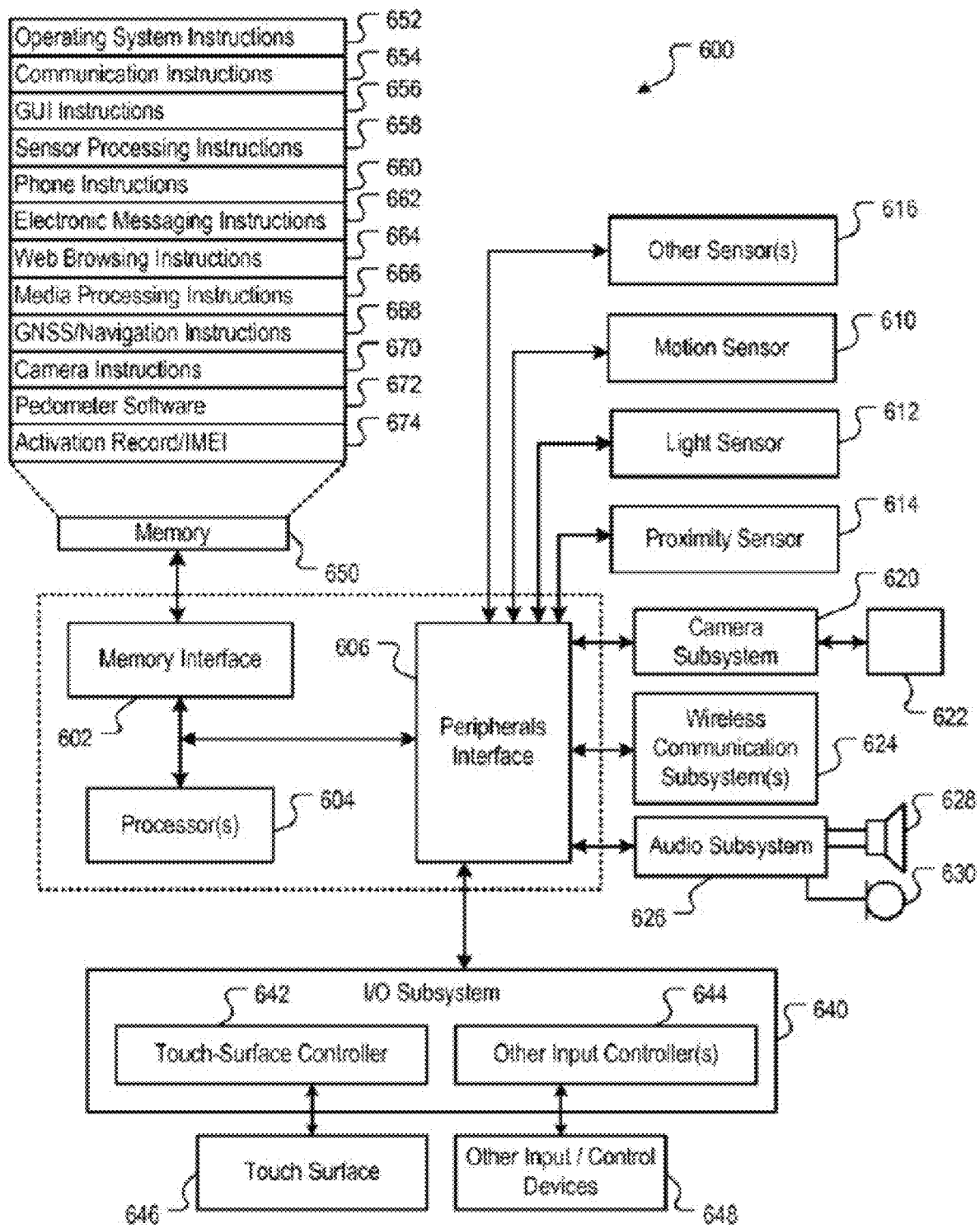
FIG. 6 illustrates a mobile device architecture that may be utilized to implement the various features and processes described herein, according to an embodiment.

FIG. 6 illustrates an embodiment of a mobile device architecture that may be utilized to implement the various features and processes described herein. Architecture 600 can be implemented in any number of portable devices including but not limited to smart wearable devices. Architecture 600 as illustrated in FIG. 6 includes memory interface 602, processors 604, and peripheral interface 606. Memory interface 602, processors 604 and peripherals interface 606 can be separate components or can be integrated as a part of one or more integrated circuits. The various components can be coupled by one or more communication buses or signal lines.

Processors 604 as illustrated in FIG. 6 are meant to be inclusive of data processors, image processors, central processing unit, or any variety of multi-core processing devices. Any variety of sensors, external devices, and external subsystems can be coupled to peripherals interface 606 to facilitate any number of functionalities within the architecture 600 of the exemplar mobile device. For example, motion sensor 610, light sensor 612, and proximity sensor 614 can be coupled to peripherals interface 606 to facilitate orientation, lighting, and proximity functions of the mobile device. For example, light sensor 612 could be utilized to facilitate adjusting the brightness of touch surface 646. Motion sensor 610, which could be exemplified in the context of an accelerometer or gyroscope, could be utilized to detect movement and orientation of the mobile device.

Display objects or media could then be presented according to a detected orientation (e.g., portrait or landscape).

Other sensors could be coupled to peripherals interface 606, such as a temperature sensor, a biometric sensor, or other sensing device to facilitate corresponding functionalities. Location processor 615 (e.g., a global positioning transceiver) can be coupled to peripherals interface 606 to allow for generation of geo-location data thereby facilitating geo-positioning. An electronic magnetometer 616 such as an integrated circuit chip could in turn be connected to peripherals interface 606 to provide data related to the direction of true magnetic North whereby the mobile device could enjoy compass or directional functionality. Camera subsystem 620 and an optical sensor 622 such as a charged coupled device (CCD) or a complementary metal-oxide semiconductor (CMOS) optical sensor can facilitate camera functions such as recording photographs and video clips.

Communication functionality may be facilitated through one or more communication subsystems 624, which may include one or more wireless communication subsystems. Wireless communication subsystems 624 can include 802.5 or Bluetooth transceivers as well as optical transceivers such as infrared. Wired communication system can include a port device such as a Universal Serial Bus (USB) port or some other wired port connection that can be used to establish a wired coupling to other computing devices such as network access devices, personal computers, printers, displays, or other processing devices capable of receiving or transmitting data. The specific design and implementation of communication subsystem 624 may depend on the communication network or medium over which the device is intended to operate. For example, a device may include wireless communication subsystem designed to operate over a global system for mobile communications (GSM) network, a GPS network, an enhanced data GSM environment (EDGE) network, 802.5 communication networks, code division multiple access (CDMA) networks, or Bluetooth networks. Communication subsystem 624 may include hosting protocols such that the device may be configured as a base station for other wireless devices. Communication subsystems can also allow the device to synchronize with a host device using one or more protocols such as TCP/IP, HTTP, or UDP.

Audio subsystem 626 can be coupled to a speaker 628 and one or more microphones 630 to facilitate voice-enabled functions. These functions might include voice recognition, voice replication, or digital recording. Audio subsystem 626 in conjunction may also encompass traditional telephony functions.

I/O subsystem 640 may include touch controller 642 and/or other input controller(s) 644. Touch controller 642 can be coupled to a touch surface 646. Touch surface 646 and touch controller 642 may detect contact and movement or break thereof using any of a number of touch sensitivity technologies, including but not limited to capacitive, resistive, infrared, or surface acoustic wave technologies. Other proximity sensor arrays or elements for determining one or more points of contact with touch surface 646 may likewise be utilized. In one implementation, touch surface 646 can display virtual or soft buttons and a virtual keyboard, which can be used as an input/output device by the user.

Other input controllers 644 can be coupled to other input/control devices 648 such as one or more buttons, rocker switches, thumb-wheels, infrared ports, USB ports, and/or a pointer device such as a stylus. The one or more buttons (not shown) can include an up/down button for volume control of speaker 628 and/or microphone 630. In some implementations, device 600 can include the functionality of an audio and/or video playback or recording device and may include a pin connector for tethering to other devices.

Memory interface 602 can be coupled to memory 650. Memory 650 can include high-speed random access memory or non-volatile memory such as magnetic disk storage devices, optical storage devices, or flash memory. Memory 650 can store operating system 652, such as Darwin, RTXC, LINUX, UNIX, OS X, ANDROID, WINDOWS, or an embedded operating system such as VXWorks. Operating system 652 may include instructions for handling basic system services and for performing hardware dependent tasks. In some implementations, operating system 652 can include a kernel.

Memory 650 may also store communication instructions 654 to facilitate communicating with other mobile computing devices or servers. Communication instructions 654 can also be used to select an operational mode or communication medium for use by the device based on a geographic location, which could be obtained by the GPS/Navigation instructions 668. Memory 650 may include graphical user interface instructions 656 to facilitate graphic user interface processing such as the generation of an interface; sensor processing instructions 658 to facilitate sensor-related processing and functions; phone instructions 660 to facilitate phone-related processes and functions; electronic messaging instructions 662 to facilitate electronic-messaging related processes and functions; web browsing instructions 664 to facilitate web browsing-related processes and functions; media processing instructions 666 to facilitate media processing-related processes and functions; GPS/Navigation instructions 668 to facilitate GPS and navigation-related processes, camera instructions 670 to facilitate camera-related processes and functions; and instructions 672 for any other application that may be operating on or in conjunction with the mobile computing device. Memory 650 may also store other software instructions for facilitating other processes, features and applications, such as applications related to navigation, social networking, location-based services or map displays.

Figure 7A:
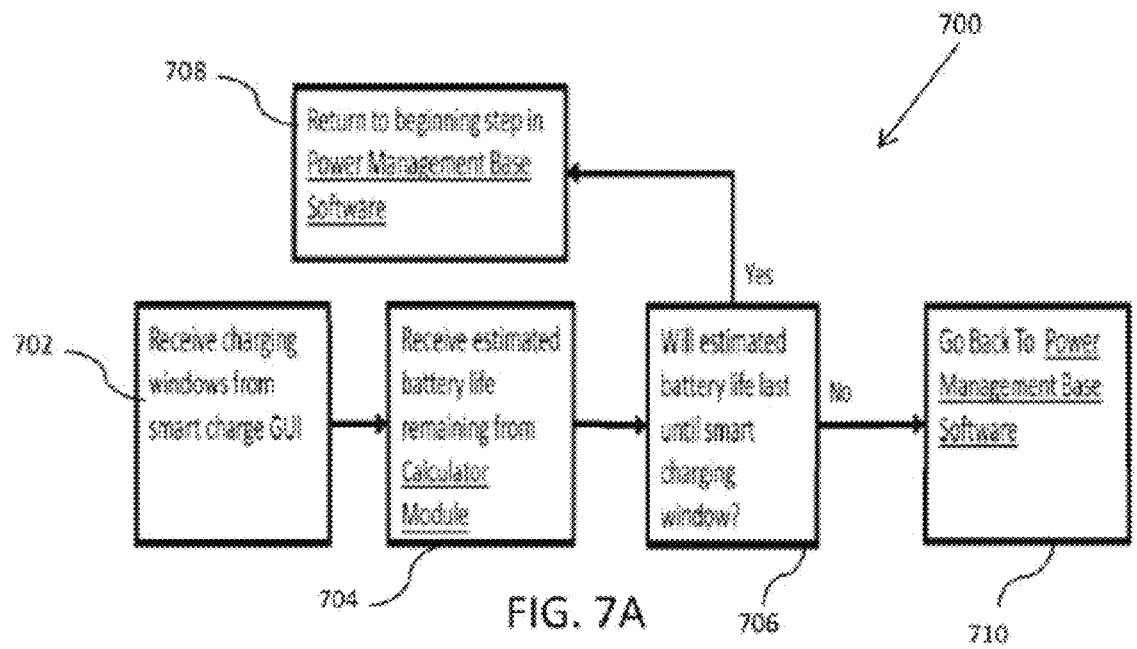
FIG. 7A is a flowchart of an algorithm that may be implemented by a software prediction module, according to an embodiment.

Referring to FIG. 7A, in one embodiment, is an example of a method 700 (i.e. an algorithm) that may be implemented by software prediction module. The prediction model flowchart begins with step 702 where one or more charging windows are received from a smart charge GUI. In an alternate embodiment, an estimated next charging time (or window) may be received, wherein the estimated charging window is estimated according to known user habits or activity as performed over time. Next, in step 704, an estimate of remaining battery life may be received from the calculator module. The remaining battery life may be determined according to current usage, average usage over a particular period of time, average battery consumption over time, or according to other methods as are known in the art. Next, in step 706, remaining estimated battery life is compared to see if it will last until the next smart charging window. If yes, program flow may move to an initial (beginning) step in the power management base software, in step 708. If no, (i.e. battery life is predicted not to last until the next smart charging window), program flow may move to a recommendations module in step 710, as depicted in FIG. 7B.

Figure 7B:
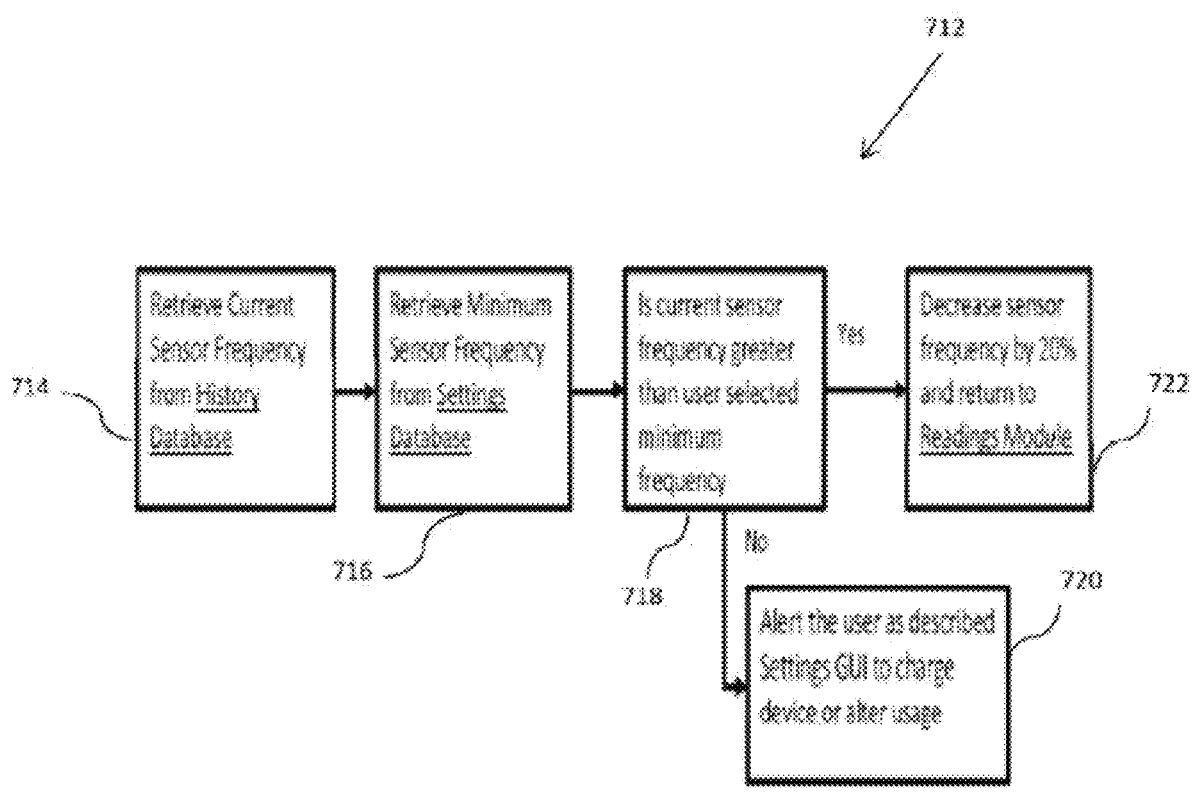
FIG. 7B is a flowchart of an algorithm that may be implemented by a recommendations module, according to an embodiment.

Referring to FIG. 7B, in one embodiment, is an example of a method 712 (i.e. algorithm) that may be implemented by a recommendations module. The recommendations module of FIG. 7B begins, in an embodiment, in step 714 that retrieves a current sensor frequency setting from a history database. At step 716 the recommendation module retrieves a minimum sensor frequency setting from the settings database. At step 718 of the flow chart it is determined whether the current settings are greater than the user selected minimum frequency. If the current sampling rate is greater than the user-defined minimum, program flow may move to step 720 that sends an alert to the user that indicates that the user should charge the wearable device 102 or change (alter) the minimum frequency. When the current sensor reading is greater than the minimum selected frequency the recommendations module software may decrease the sampling frequency by 20% (or down to the minimum) at step 722 and then program flow moves back to the running the readings module software.

In an alternate embodiment, the system or device may employ an artificial intelligence (e.g. a deep-learning engine or neural network) that learns best frequencies or charging times for a particular user and/or for particular times.

Figure 8:
FIG. 8 is a table of data that may be stored in a history database, according to an embodiment.

FIG. 8 illustrates an embodiment of data that may be stored in a table 800 in a history database 126. The table includes column headers of time, sensor 1 pulse, battery level, and battery level calculation data. The table cross-references a time, a measurement of a pulse that was sensed at the time, a battery level, and the result of a calculation that identifies how long the battery is predicted to run at a current level of power use. A first row in the table indicates that at 8 AM a user of the wearable device 102 had a pulse rate of 81 beats per minute (BPM), a battery level of 90%, and an estimated remaining battery life of 8 hours. Note as time goes by the battery level and estimate of remaining battery life decrease.

Figures 9A, 9B:
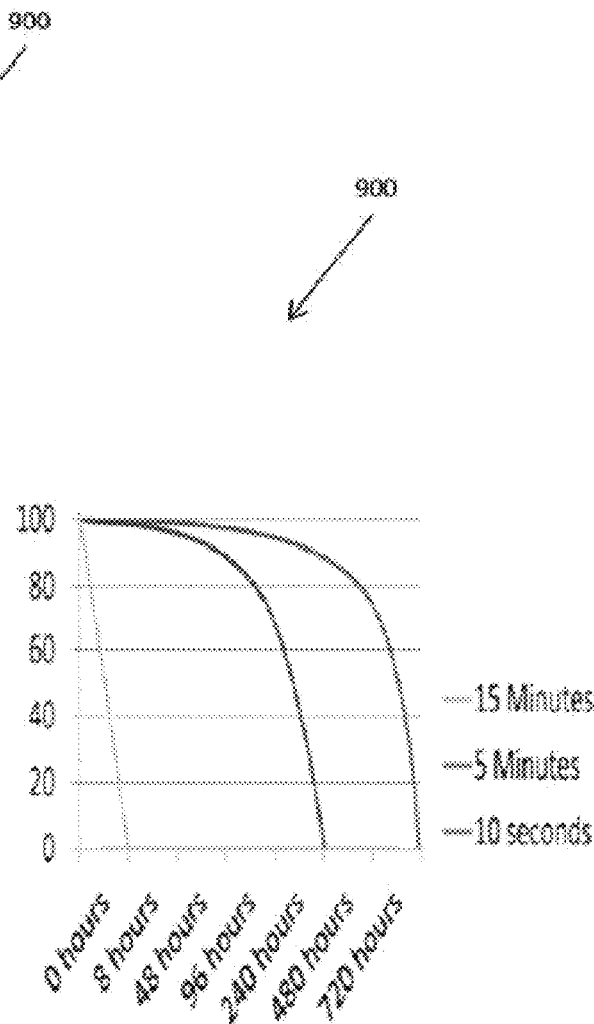
FIG. 9A is a table of data that may be stored in a settings database, according to an embodiment.
FIG. 9B is a graph having three plots representing how long a battery may last when sensors are sampled at different frequencies, according to an embodiment.

FIG. 9A illustrates an embodiment of data that may be stored in a table 900 in a settings database 122, and FIG. 9B is a graph depicting how long the battery should last when sensors are sampled at different frequencies. The table in FIG. 9A includes column header of pulse sensor frequency, battery life estimate, and user settings. According to this embodiment, a maximum sample frequency of the pulse sensor is 10 seconds, a default setting is 5 minutes, and a minimum setting is 15 minutes. The table also includes a current battery life setting of max, and an alert type of text. The plots of the graphs depicted in FIG. 9B illustrate how quickly the energy in the battery should change over time. When the battery life is predicted to not last until a next charge cycle, a text message may be sent to the mobile device of the user informing the user to charge the wearable device 102 or change a setting.

FIG. 10 illustrates an embodiment of settings that may be saved in a table 1000 in a smart charging database. Notice that Monday, Wednesday, and Friday have a charging window setting from 6:00 PM to 8:00 PM. Notice also that Tuesday, Thursday, Saturday, and Sunday do not have a charging window setup in the table.

Figure 11:
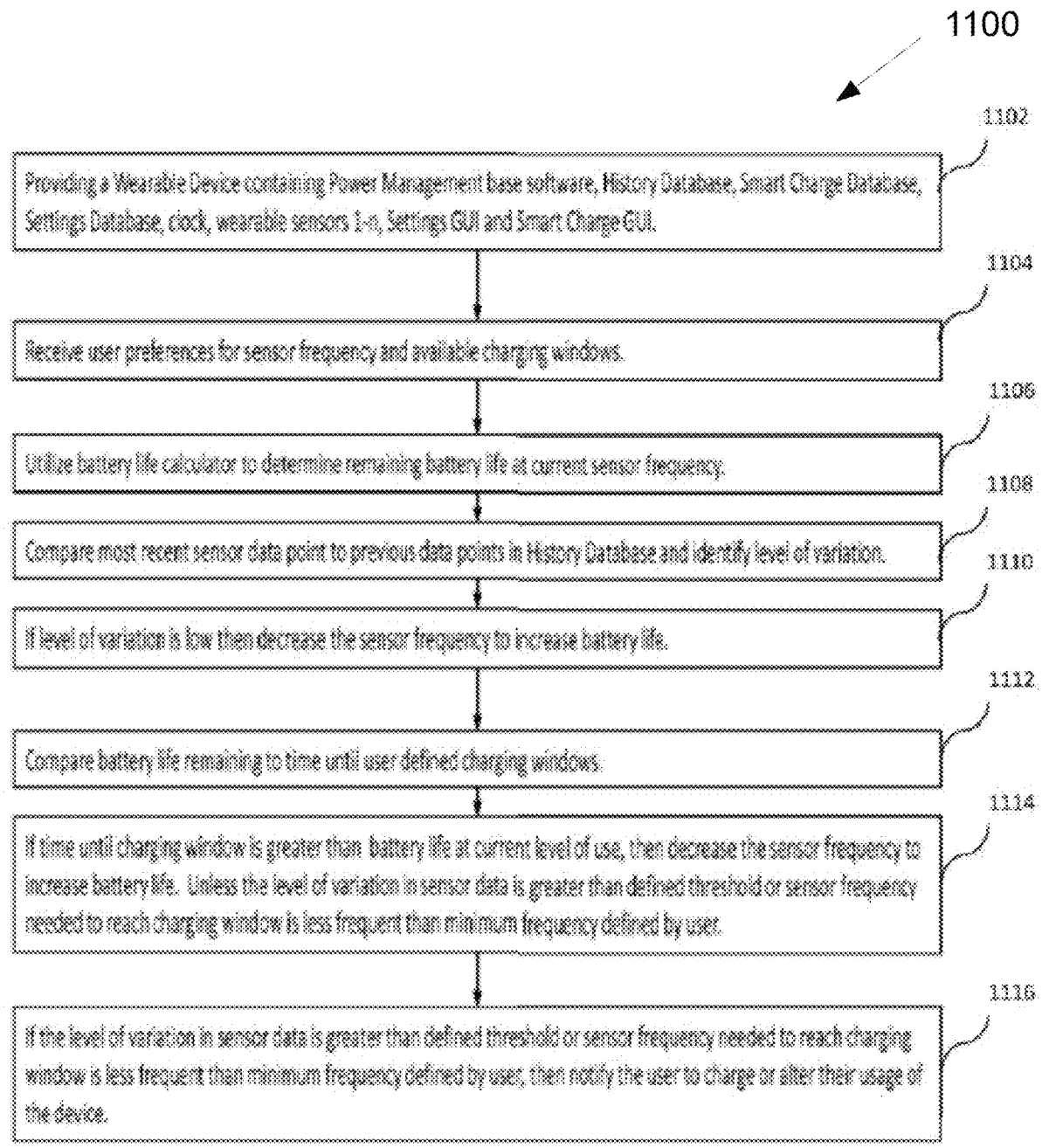
FIG. 11 is a method for monitoring and adjusting a sample rate of sensor data from a sensor in order to limit power consumption, according to an embodiment.

FIG. 11 illustrates an embodiment of a method (i.e., algorithm) 1100 for managing the power consumption of a sensor (e.g. sensor 104) in a wearable device 102. One of ordinary skill will appreciate, in conjunction with a review of this disclosure, that the steps of the above methods may be combined in any number of ways that advantageously results in more efficient use of the sensors, according to use requirements and expected charging times.

In an embodiment, at step 1102, where a wearable device 102 is provided. The wearable device 102 may be any of the wearable device 102 embodiments described or otherwise envisioned herein. For example, including power management base software 120, a history database 126, a smart charge database 124, a settings database 122, a clock 114, wearable sensors 1-N, a settings GUI 128, and a smart charge GUI 130. The wearable device 102 may be, for example, the embodiment of the device 102 described in conjunction with FIG. 1, among other embodiments.

At step 1104, preferences may be received from user that may identify sensor frequencies and identify one or more charging windows. This calculation may alternately be described as determining the length of time till next charge. In an alternate embodiment, charging windows (time till next charge) may be estimated from historical use.

At step 1106, a battery life calculator may calculate (determine) an estimate of remaining battery life at the current sensor sampling frequency.

At step 1108, recent sensor data may be compared with a plurality of previous sensor data points (or values derived from a plurality of data points) when identifying a level of variation (i.e. percentage change) in the sensor measurements or values.

At step 1110, of the method, according to an embodiment, the sensor frequency may be decreased to save power when the level of sensor measurement variation is low.

At step 1112, the estimated battery life may be compared with a charging window (or time until next charging window) when determining whether the battery has enough power to last until the next charging window. If the battery life is estimated to run out before the next charging window, the sensor frequency may be decreased in order to increase battery life. If, however, the level of variation in sensor data is greater than defined threshold, or the sensor frequency needed to reach the next charging window is less frequent than minimum the current sensor sampling frequency may be maintained or increased as use requires and according to various embodiments.

Finally, at step 1114 of FIG. 11 and according to an embodiment, when the level of variation in sensor data is greater than a defined threshold, or when the sensor frequency needed to reach the next charging window is less frequent than minimum frequency defined by user, the user of the wearable device 102 may be sent a message informing the user to charge or change (alter) setting in their wearable device 102, at step 1116. For example, if the level of variation is greater than a 5% threshold, the user may be notified that the battery will not last until the next defined (estimated) charging window, and thus the user should reduce activity or alter the settings to allow for a lower sampling rate. In another example, if the minimum frequency is set such that, even at the minimum frequency, the battery will not last until the next charging window, the user may be notified to change the minimum frequency so that the battery will last until the next window.

Various interfaces may be implemented—both communications and interface. One skilled in the art will appreciate the various requisite components of a mobile device and integration of the same with one or more of the foregoing figures and/or descriptions.

While various embodiments have been described above, it should be understood that they have been presented by way of example only, and not limitation. The descriptions are not intended to limit the scope of the invention to the particular forms set forth herein. Thus, the breadth and scope of a preferred embodiment should not be limited by any of the above-described embodiments. It should be understood that the above description is illustrative and not restrictive. To the contrary, the present descriptions are intended to cover such alternatives, modifications, and equivalents as may be included within the spirit and scope of the invention as defined by the appended claims and otherwise appreciated by one of ordinary skill in the art.

The scope of the invention should, therefore, be determined not with reference to the above description, but instead should be determined with reference to the appended claims along with their full scope of equivalents. All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be examples and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for monitoring power consumption by a wearable device, the method comprising the steps of:
  receiving a plurality of sensor readings from a sensor of the wearable device, wherein the plurality of sensor readings are obtained at a first sampling frequency;
  determining, by a processor of the wearable device, at least a first sensor value of a first sensor reading and a second sensor value of a second sensor reading from the plurality of sensor readings, wherein the second sensor reading is obtained after the first sensor reading;
  calculating a difference between the first and second sensor values; and
  varying the first sampling frequency of the sensor according to the calculated difference,
  wherein the first sampling frequency is increased if the difference is above a predetermined threshold and the second sensor value is greater than the first sensor value, and wherein the first sampling frequency is decreased if the difference is above the predetermined threshold and the second sensor value is less than the first sensor value.

2. The method of claim 1, wherein the first sensor value is a magnitude of a first sensor reading of the plurality of sensor readings and the second sensor value is a magnitude of a second reading of the plurality of sensor readings.

3. The method of claim 1, wherein the first sensor value is a time elapsed between a first event measured by the plurality of sensor readings and a second event measured by the plurality of sensor readings, and the second sensor value is a time elapsed between a third event measured by the plurality of sensors readings and a fourth event measured by the plurality of sensor readings.

4. The method of claim 1, further comprising the steps of:
  estimating remaining charge time of a battery of the wearable device;
  comparing the estimated remaining charge time to a time until a next scheduled recharge; and
  decreasing a sampling rate of the sensor if the remaining charge time is less than the time until the next scheduled recharge.

5. The method of claim 4, wherein the time until next charge is calculated according to a next charge time received from a user.

6. The method of claim 4, further comprising the steps of: notifying the user to charge or alter their usage of the wearable device if the level of variation is greater than a user-defined threshold or if a suggested sensor frequency does not fall within a user-defined frequency range.

7. A non-transitory computer readable storage medium having embodied thereon a program executable by a processor to perform an algorithm, the algorithm comprising the steps of:
receiving a plurality of sensor readings from a sensor of the wearable device, wherein the plurality of sensor readings are obtained at a first sampling frequency;
determining, by a processor of the wearable device, at least a first sensor value of a first sensor reading and a second sensor value of a second sensor reading from the plurality of sensor readings, wherein the second sensor reading is obtained after the first sensor reading;
calculating a difference between the first and second sensor values; and
varying the first sampling frequency of the sensor according to the calculated difference,
wherein the first sampling frequency is increased if the difference is above a predetermined threshold and the second sensor value is greater than the first sensor value, and wherein the first sampling frequency is decreased if the difference is above the predetermined threshold and the second sensor value is less than the first sensor value.

8. The non-transitory computer readable storage medium of claim 7, wherein the first value is a magnitude of a first sample of the plurality of sensor samples and the second value is a magnitude of a second sample of the plurality of sensor samples.

9. A system for monitoring power consumption by a wearable device comprising:
at least one sensor of the wearable device;
a processor having executable instructions thereon configured to cause the processor to:
receive a plurality of sensor readings from the at least one sensor, wherein the plurality of sensor readings are obtained at a first sampling frequency;
determine at least a first sensor value of a first sensor reading and a second sensor value of a second sensor reading from the plurality of sensor readings, wherein the second sensor reading is obtained after the first sensor reading;
calculate a difference between the first and second sensor values; and
vary the first sampling frequency of the sensor according to the calculated difference,
wherein the first sampling frequency is increased if the difference is above a predetermined threshold and the second sensor value is greater than the first sensor value, and wherein the first sampling frequency is decreased if the difference is above the predetermined threshold and the second sensor value is less than the first sensor value.

10. The system of claim 9, wherein the first value is a magnitude of a first sample of the plurality of sensor samples and the second value is a magnitude of a second sample of the plurality of sensor samples.

11. The system of claim 9, wherein the executable instructions are further configured to cause the processor to:
estimate remaining charge time of a battery of the wearable device;
compare the estimated remaining charge time to a time until a next scheduled recharge; and
decrease a sampling rate of the sensor upon determining that the remaining charge time is less than the time until the next charge.

12. The system of claim 11, wherein the time until next charge is calculated according to a next charge time received from a user.

13. The system of claim 11, wherein the executable instructions are further configured to cause the processor to: notify a user to charge or alter their usage of the wearable device if a level of variation is greater than a user-defined threshold or if the suggested first sampling frequency does not fall within a user-defined frequency range.

* * * * *